United States Patent [19]

Mattingly, III et al.

[11] Patent Number: 4,690,679
[45] Date of Patent: Sep. 1, 1987

[54] COEXTRUDED APERTURED FILM SANITARY NAPKIN COVER

[75] Inventors: William B. Mattingly, III, Somerset; Alex W. Cabe, Jr., Lebanon; Richard B. Chapas, E. Windsor; Arthur J. Sampson, Jr., Belle Mead, all of N.J.

[73] Assignee: Johnson & Johnson, New Brunswick, N.J.

[21] Appl. No.: 840,290

[22] Filed: Mar. 14, 1986

[51] Int. Cl.⁴ .............................................. A61F 13/16
[52] U.S. Cl. .................................................. 604/383
[58] Field of Search ................... 604/383, 385.1, 371, 604/370, 366

[56] References Cited

U.S. PATENT DOCUMENTS

| | | | |
|---|---|---|---|
| 3,843,478 | 10/1974 | Zuscik | 161/164 |
| 3,888,248 | 10/1975 | Moore et al. | 604/383 |
| 3,965,906 | 6/1976 | Karami | 604/383 |
| 3,994,299 | 11/1976 | Karami | 604/383 |
| 4,315,507 | 2/1982 | Whitehead et al. | |
| 4,324,246 | 4/1982 | Mullane et al. | |
| 4,381,326 | 4/1983 | Kelly | 428/134 |
| 4,463,045 | 7/1984 | Ahr et al. | 428/131 |

Primary Examiner—John D. Yasko
Attorney, Agent, or Firm—Lawrence D. Schuler

[57] ABSTRACT

An apertured film, suitable for use as a sanitary napkin cover which passes body fluids, is provided. The film comprises a first layer of a first polymeric material and a second layer of a second polymeric material. Both layers are apertured for the transmission of body fluids therethrough. The first polymeric material exhibits a melting point temperature which is greater than the melting point temperature exhibited by the second polymeric material. The apertured film may be thermally bonded by heating the film to a temperature in excess of the melting point temperature of the second layer material and below the melting point temperature of the first layer material. The unmelted first layer will thereby maintain the integrity of the apertured film when the second layer is in its thermally softened condition.

22 Claims, 8 Drawing Figures

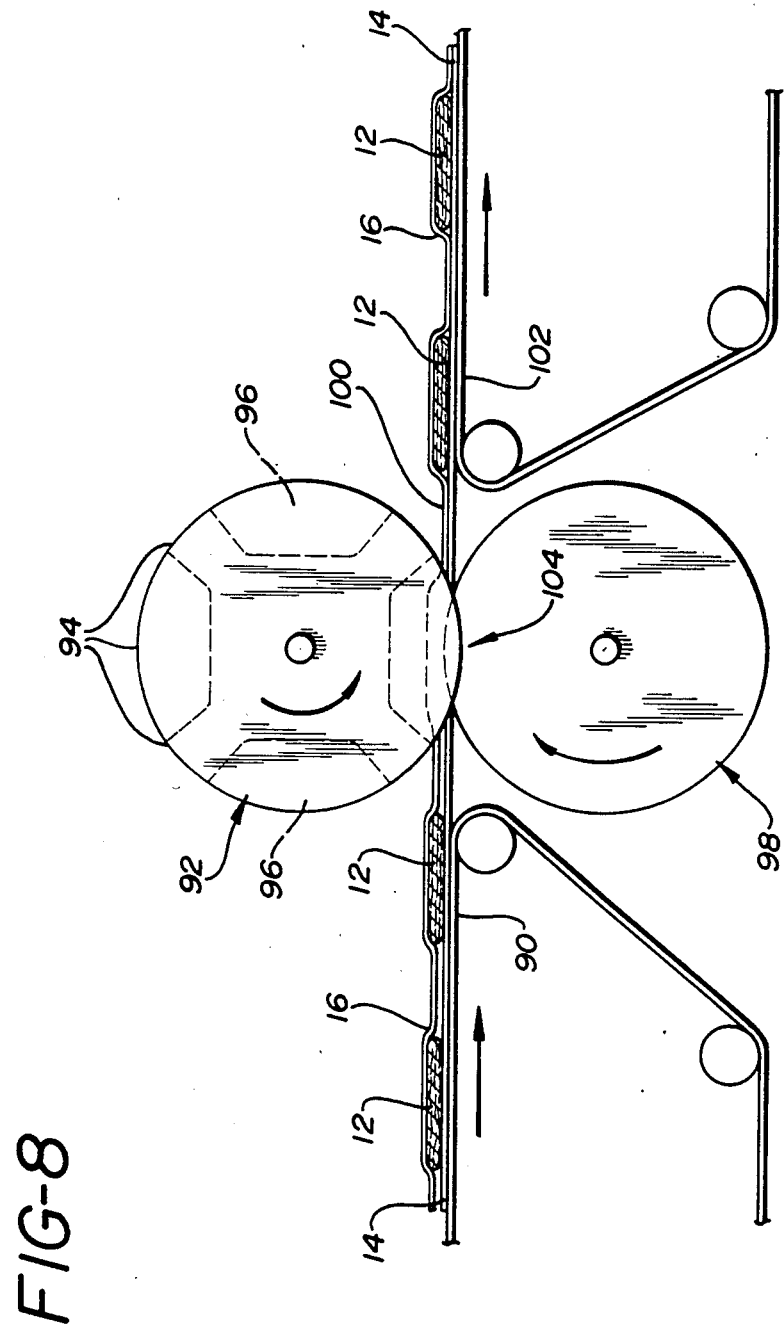

COEXTRUDED APERTURED FILM SANITARY NAPKIN COVER

This invention relates to absorbent products such as diapers, sanitary napkins, wound dressings and the like and, in particular, to such products having coextruded apertured film covers.

In general, such products have an absorbent core comprising one or more layers of fluid absorbent material such as wood pulp, rayon, gauze, tissue or the like, and in some cases synthetic hydrophilic material such as hydrophilic polyurethane foam may be used. The hydrophilic material is generally provided in the form of a pad, which may have a rectangular or somewhat oval shape. To protect the clothing of the user from being stained or wetted by the body fluids absorbed by the hydrophilic material, the pad is generally backed by a body fluid impervious barrier sheet. The absorbent product is positioned on the body with the hydrophilic material facing the body and the fluid impervious barrier facing the clothing of the user.

To enhance the sense of comfort for the user, absorbent products also generally employ a cover material or facing which covers the body-facing surface of the hydrophilic material. The purpose of the cover is to structurally contain the loosely packed absorbent material and to protect the body from direct contact with the absorbent pad. The cover is pervious to body fluids on the side of the product that is placed against the body, and is preferably relatively nonabsorbent so as to promote the transfer of body fluids to the absorbent pad with minimal fluid retention by the cover. The fluid pervious characteristic may be obtained by use of an apertured film cover, for instance. A well designed cover will thus remain relatively dry in use, thereby increasing the comfort of the user.

The cover material should desirably exhibit several other favorable characteristics. The body-contacting surface of the cover should feel soft and velvety to the touch. In addition to softness, the cover should be smooth. Certain visual characteristics are also desirable such as the coloring and luster of the outer surface.

Additionally, some means must be provided for affixing the cover in its desired position on the product. One technique for affixing the cover is to wrap the edges of the cover onto the barrier sheet on the back of the product and adhesively attach the cover to the barrier sheet where the two overlie each other. However, this technique adds several steps and additional equipment to the manufacturing process, as the adhesive must first be applied by way of some applicator mechanism and then be allowed to dry or cure. A more preferred technique for affixing the cover is to heat seal it to the product. While heat sealing requires its own specialized process apparatus, it does not require any additional substances such as adhesives, and it eliminates the need for time to cure.

Heat sealing presents its own problems, however. It is possible for heat sealing to leave a relatively hard or rough surface at the heat-sealed jointure, which will undesirably reduce the softness of the absorbent product and detract from its aesthetic appearance. In the case of an apertured film cover, the film can become distended or irregular in appearance where it is melted for heat sealing, which will further detract from the comfortable appearance and visual aesthetics of the product. Moreover, exposure to heat during any part of the process can result in closure of the apertures.

In accordance with the principles of the present invention, a cover is provided for an absorbent product having the aforementioned desirable characteristics. The cover comprises an apertured polymeric film material, including an upper layer, intended to be placed against the body, comprising a first polymeric material and a lower layer, placed against an absorbent core, comprising a second polymeric material. The upper layer comprises a polymer having a higher melting point than that of the polymer comprising the lower layer. The cover further comprises a multiplicity of small apertures which render the cover pervious to body fluids. When the cover is thermally bonded to the barrier sheet, back cover, or other material, the lower layer will melt to form the thermal bond. The upper layer will not melt and provides structural integrity for the apertured cover while the lower layer is in its thermally softened condition. Thus, thermal bonding may be accomplished without disrupting the appearance or tactile characteristics of the cover, particularly those of its upper layer.

In a preferred embodiment, the upper layer of the cover includes calcium carbonate as a delustrant, i.e. a material which substantially eliminates or greatly reduces the gloss or shiny appearance otherwise characteristic of the polymer comprising the upper layer, and the lower layer includes titanium dioxide as an opacifier. The upper layer is substantially free of the titanium dioxide opacifier and the lower layer is substantially free of the calcium carbonate delustrant.

Figure 5:
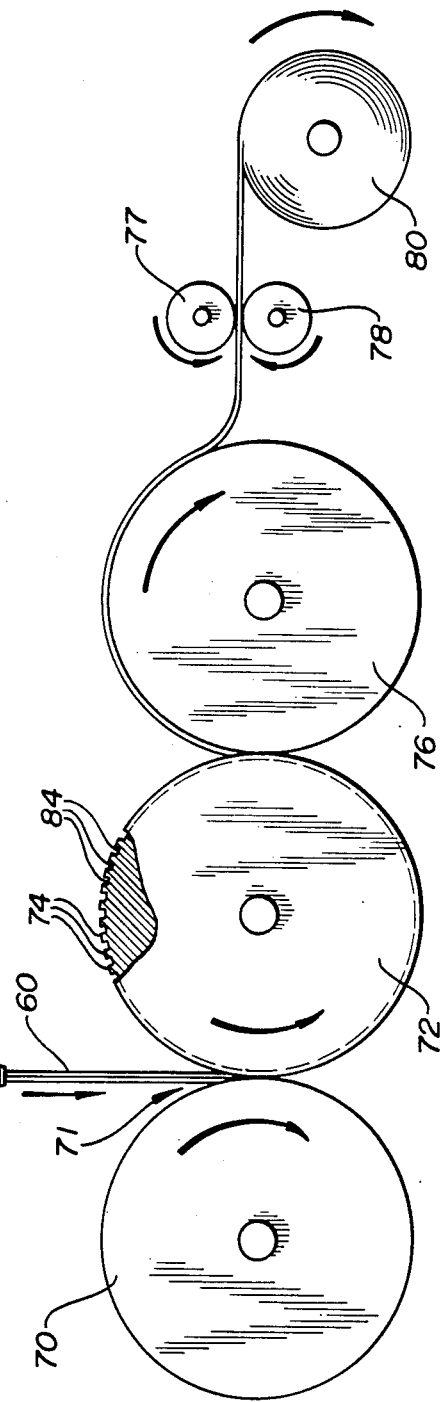
Figure 6:
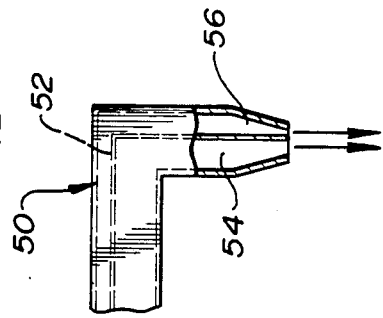
Figure 7:
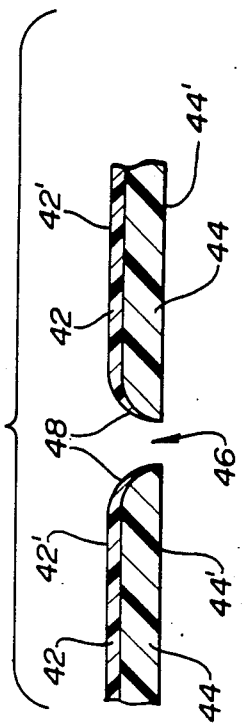

FIGS. 5 and 6 schematically illustrate processing apparatus for producing an apertured film cover in accordance with the principles of the present invention;

FIG. 7 is a cross-sectional view of an apertured film cover constructed in accordance with the principles of the present invention; and FIG. 8 schematically illustrates a heat-sealing process for sanitary napkins.

Figure 1:
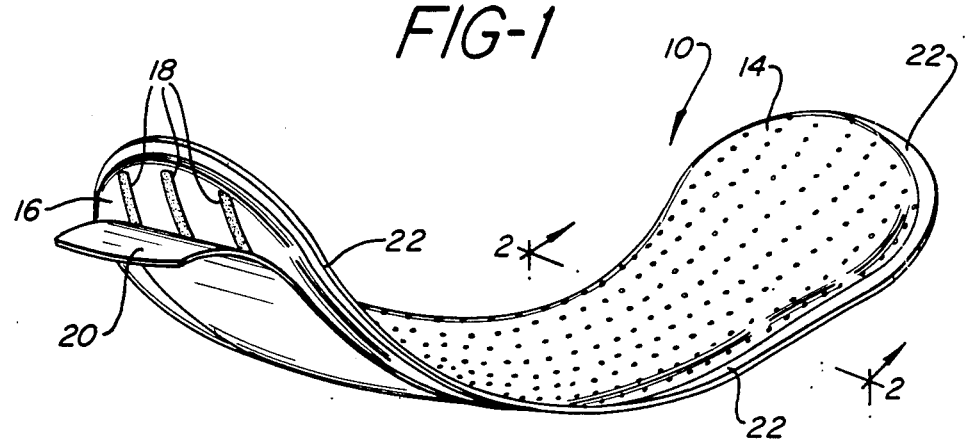
FIG. 1 is a perspective view of a sanitary napkin constructed in accordance with the principles of the present invention.
Figure 2:
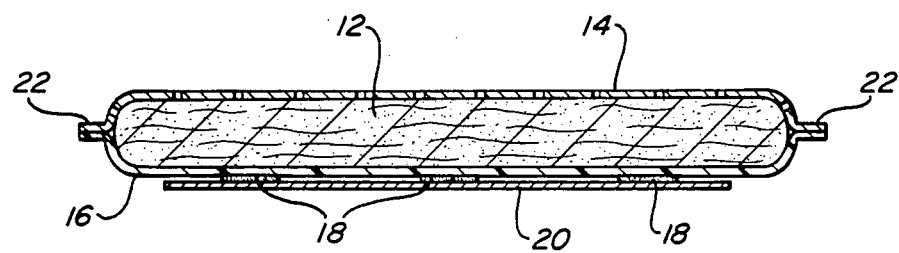
FIG. 2 is a cross-sectional view of the sanitary napkin of FIG. 1.

Referring concurrently to FIGS. 1 and 2, a sanitary napkin 10 constructed in accordance with the principles of the present invention is shown. The napkin 10 has a generally oval, hourglass-shape, being narrower in the center so as to provide comfort in the crotch area of the user. Body fluids are absorbed and retained by an absorbent pad 12, shown in FIG. 2, which is sealed between an apertured film cover 14 and a fluid impervious barrier 16. The absorbent pad 12 may be comprised of any of the well known absorbents such as wood pulp, rayon, synthetic absorbents in the form of fibers, powder, or foam or combinations thereof. Absorbency enhancers such as the so called "super absorbent" materials may be employed. Non-hydrophilic materials may also be employed in combination with absorbent materials. One such example is low density, thermal bonded nonwoven fabric comprising a mixture of absorbent fibers and staple length polyester/polyethylene conjugate fibers. The absorbent fibers may be wood pulp or other cellulosic fibers which may have been treated to enhance absorbency. Suitable conjugate fibers are fibers which comprise a polyester core surrounded by a sheath of polyethylene. A highly satisfactory absorbent pad is produced by a thermally bonded absorbent fabric comprising 54% by weight of wood pulp fibers and 46% by weight of conjugate fibers having a staple length of 3.81 cm. and a denier of 3.0. The fabric is stabilized by passing hot air through the fibers and thereby melting the polyethylene which bonds the fibers together upon cooling. Such a fabric is capable of holding about 17 times its own weight of distilled water. Alternatively, an absorbent pad of densified web material may be employed, as described in U.S. Pat. No. 4,551,142.

The fluid impervious barrier 16 acts as a barrier to body fluids and prevents staining of the undergarments of the user. The barrier may comprise any thin flexible body fluid impermeable material such as a polymeric film, e.g., polyethylene, polypropylene, cellophane. Alternatively, the barrier may comprise a normally fluid pervious material that has been treated to be impervious such as impregnated fluid repellant paper. If desired, the barrier 16 may be adhesively affixed to the garment facing side of the absorbent pad 12.

Disposed on the garment facing surface of the barrier 16 are longitudinally extending pressure-sensitive adhesive means 18, provided for attaching the napkin to the crotch portion of an undergarment. While such adhesive means are illustrated in the form of longitudinally extending lines, it will be understood that various patterns such as spots or transverse lines are suitable. The adhesive employed may be any of the large number of pressure-sensitive adhesives that are commercially available, including water based adhesives such as acrylate adhesives. e.g., vinyl acetate/2-ethylhexyl acrylate copolymer which may be combined with tackifiers. Alternatively, the adhesive may also comprise a pressure sensitive rapid-setting hot melt adhesive. The adhesive element may also comprise a double faced tape.

Overlying the adhesive means 18 is a protective release strip 20 which is provided to protect the adhesive means from dirt and unintended adhesion prior to use. The release strip 20 may be constructed of any suitable sheet-like material which adheres with sufficient tenacity to the adhesive means to remain in place prior to use but which can be readily removed when the napkin is to be used. A particularly useful material is a semibleached kraft paper, the adhesive contacting side of which has been silicone treated to provide easy release from the adhesive means 18.

In a specific embodiment of an apertured film found useful as a sanitary napkin cover, the apertures had an average equivalent circular diameter of about 0.016 inches and an average center-to-center spacing of about 0.028 inches. The same specific embodiment had an average open area of about 42%, a thickness of about 4.5 mils, and a weight of about one oz/yd$^2$. It will be recognized that useful cover material for sanitary napkins or like absorbent products may have other values from those mentioned above. Thus, apertured films useful for absorbent products may have weights ranging from about 0.5 oz/yd$^2$ to about 2.0 oz/yd$^2$ (preferably from 0.7 oz/yd$^2$ to 1.3 oz/yd$^2$), open areas ranging from about 20% to about 70% (preferably from about 30% to about 60%), and thicknesses ranging from about 1 to about 10 mils (preferably about 3 to 6 mils). It will be evident, when the apertured film is to be used in absorbent products, that the number, size and spacing of the apertures can be varied so long as body fluids contacting the film will be transmitted through the film to the underlying absorbent core. Apertures having average equivalent circular diameters ranging from about 0.010 inches to about 0.030 inches have been found useful in absorbent products.

Aperture sizes, percent open areas, basis weights, and thicknesses can be provided outside the above mentioned ranges where the apertured film is intended for uses in other applications such as elastic wrapping materials.

Figure 3:
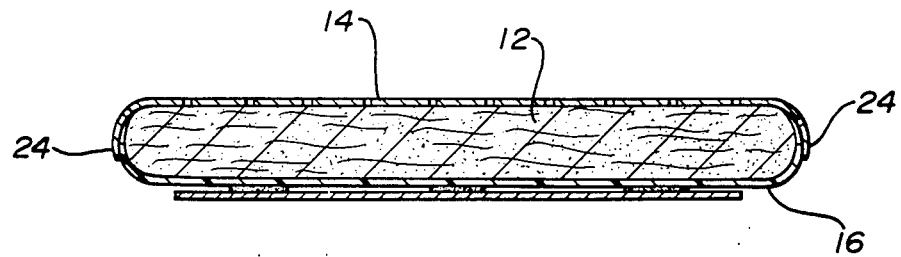
FIGS. 3 and 4 are cross-sectional views of sanitary napkins constructed using alternate techniques in accordance with the principles of the present invention.
Figure 4:
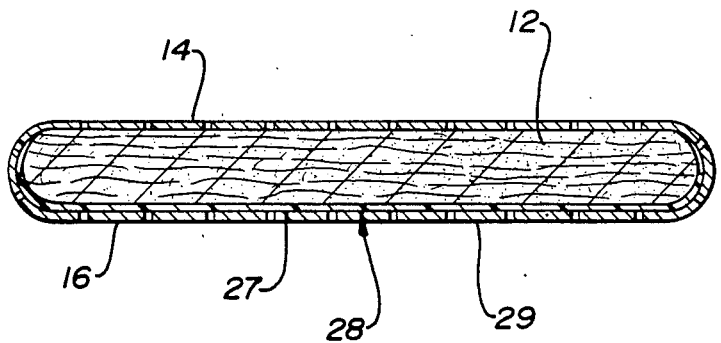

The apertured film cover 14 is thermally bonded to the barrier 16 about the periphery 22 of the napkin 10. In FIGS. 1 and 2, the bonded periphery 22 is seen to outwardly extend from the napkin. Alternatively, the barrier 16 may be folded upward about the edges of the absorbent pad 12, and the cover 14 folded over the barrier edges and thermally bonded at the overlap 24, as shown in FIG. 3. This technique gives the edges of the napkin a more rounded and comfortable appearance. In other absorbent product applications, it may be desirable to completely enclose the absorbent pad 12 in an apertured film cover, as shown in FIG. 4. In this embodiment, the cover 14 surrounds the absorbent pad 12 and the barrier 16, with the edges of the cover adjoining each other at a seam indicated at 28. On either side of the seam the cover is thermally bonded to the underlying barrier 16, as indicated at 27 and 29. At the longitudinal ends of the napkin the product may be sealed by thermally bonding the edge of the body facing side of the cover to the edge of the garment facing side of the cover.

In accordance with the principles of the present invention, the apertured film cover 14 comprises a two layer apertured film, preferably formed by the coextrusion of two polymers. In the preferred embodiment, shown in an enlarged cross-section in FIG. 7, the body-facing top layer 42, which forms the outer surface of the napkin, has different characteristics from the bottom layer 44. The top layer 42 is smooth with a fabric-like appearance. The bottom layer 44 provides the heat sealability for the cover. The polymers of both layers should be flexible. They should exhibit a flexural modulus of less than 350,000 pounds per square inch (p.s.i.) by the ASTM Method D-638, more preferably less than 100,000 p.s.i., and most preferably less than 50,000 p.s.i. The two polymers should also be chosen so that the tensile strength of the cover is at least 0.5 lbs/inch width in the machine direction (MD) and 0.3 lbs/inch width in the cross direction (CD). More preferable would be for the material to exhibit an MD tensile strength of 0.7 lbs/inch width and a CD tensile strength of 0.5 lbs/inch width. Most preferred would be an MD tensile strength of at least about 1.0 lbs/inch width and a CD tensile strength of at least about 0.7 lbs/inch width.

The main criterion for choosing the polymers to be used for the top and bottom layers is the melting point temperature differential between any two possible polymers. Once a polymer for one layer is selected, the polymer for the other layer is chosen such that the polymer of the top layer 42 has a higher melting point than that of the bottom layer 44. As is well known, polymeric materials do not have sharply defined melting points. As used herein, the term melting point refers to the temperature at the peak of the melting endotherm, at which point the solid and liquid states are in equilibrium, as determined by a differential scanning calorimeter, such as a Perkin-Elmer DSC-2. When heat sealed at a temperature intermediate the two melting points, the top layer maintains an unmelted backbone for the cover when the bottom layer is melted for thermal sealing. The top layer will thus remain intact to provide structural integrity for the cover during the heat sealing process. Secondary considerations, such as adequate tensile strength, the surface coefficient of friction, and flexural modulus requirements may also play a part in polymer selection.

Suitable polymers for the top layer 42 include lower polyolefins having from two to four carbon atoms per repeating unit, such as polypropylene or polyethylene. Specific suitable top layer materials include low density polyethylene, linear low density polyethylene, high density polyethylene, polyester, polypropylene, nylon, ethyl acrylate ethylene copolymer, very low density polyethylene, and polybutylene. Suitable polymers for the bottom layer 44 include low density polyethylene, linear low density polyethylene, high density polyethylene polyester, ethylene vinyl acetate copolymer, ethylene methyl acrylate copolymer, ethylene acrylic acid copolymer, very low density polyethylene, ethylene ethyl acrylate copolymer, thermoplastic rubbers, and polybutylene. It will be understood that the respective polymers for the top and bottom layers of the cover are selected so as to satisfy the melting point differential requirement discussed above.

In order to provide the desired coloration for a sanitary napkin cover, some amount of an opacifier is generally added to one or both of the two layers. These may include titanium dioxide or metal colorants which may be used as opacifiers. Examples of such in the class of synthetic inorganic complex oxides are chromate colorants, molybdate colorants, iron oxides, and ferriferrocyanides. Where, as is almost universally the case, a white color is desired for the cover, titanium dioxide is greatly preferred as the opacifier. Other opacifiers may be used to provide white or any other desired color.

To reduce the gloss or sheen of the top layer 42 and give the cover a more fabric-like appearance, delustrants may be added to the top layer polymer. Typical delustrant compounds include silica and calcium carbonate.

Slip agents, such as fatty acid amides, may also be included in upper layer 42 to provide smoothness and desirable tactile impression. A suitable slip agent is available from Humko Sheffield Chemical Company, Memphis, Tenn. under the designation Kemamide E. This is an unsaturated fatty monoamide derived from erucic acid having an average molecular weight of about 335, an iodine value of about 76, an acid number of about 3.2, and a melting range of 78°-84° C. In the preferred embodiment of cover 14, the amount of slip agents present in the lower layer 44 is minimized, since they tend to interfere with the heat seal properties of that layer.

The weight ratio of upper layer 42 to lower layer 44 in the apertured film cover of the present invention ranges from 85:15 to 10:90, preferably from 50:50 to 20:80. The polymeric component(s) constitutes a major Oortion, at least about 80% by weight, of each layer 42, 44. The remainder of each layer, less than about 20% by weight, comprises selected additives such as the aforementioned delustrants, slip agents and opacifiers, as well as antioxidants and anti-block components which are generally employed in extrusion and like processes for handling polymeric resins. It will be understood that delustrants, opacifiers, slip agents and the like are commonly added to polymer melts in the form of "concentrates" which usually include a "carrier resin", most typically low density polyethylene or linear low density polyethylene. The presence of these carrier resins in each layer is acceptable provided that the aforementioned melting point differential requirement is satisfied.

In a preferred embodiment, the upper layer polymer comprises linear low density polyethylene (LLDPE) and the lower layer polymer comprises an ethylene-vinyl acetate copolymer (EVA) containing about 18% by weight vinyl acetate. The LLDPE component comprises about 29–31% of the final weight of the cover, while the EVA component comprises about 55% of the final weight of the cover. The LLDPE component provides a high tensile modulus, an acceptable surface coefficient of friction, and the necessary structural integrity. The EVA component provides softness and flexibility to the cover, and its somewhat tacky surface (i.e., relatively high coefficient of friction) improves product processability. Titanium dioxide opacifier is included in the lower layer to provide white coloration, in an amount of 4.87% by weight of the final product. The final product contains a small amount, usually about 0.03% by weight, of Irganox 1010, an antioxidant, to prevent degradation of the polymers during processing and to provide long term stability to the apertured film product. About one-third of the Irganox 1010 is included in the upper layer and the remainder in the lower layer. The apertured film cover contains about 3.52% by weight of calcium carbonate as a delustrant, all of which, in the preferred embodiment under discussion is included in the upper layer, and about 0.175% by weight of Kemamide E as a slip agent. In the preferred embodiment, all of the Kemamide E is included in the upper layer. Finally, the apertured cover contains about 6.41% by weight of low density polyethylene resin; about one-fourth of this is included as a carrier resin for the nonpolymeric components in the upper layer and the remainder as a carrier resin for the nonpolymeric components in the lower layer.

The additives to be included in the lower layer of the apertured film cover were prepared as follows. A titanium dioxide opacifier concentrate was first prepared by mixing 50 parts by weight of titanium dioxide ($TiO_2$) with 49.77 parts by weight of Petrothene NA-202, an LDPE resin having a specific gravity of 0.915 and available from U.S. Industries, Inc., Stamford, Conn. An amount of 0.23 parts by weight of Irganox 1010, an anti-oxidant commercially available from Ciba-Geigy, are then added to the $TiO_2$ mixture. The three components are then mixed in a Banbury mixer. Following Banbury mixing, the hot melt is fed to an extruder for a conventional pelletizing operation.

The additives to be included in the upper layer of the apertured film cover were prepared as follows. A calcium carbonate ($CaCO_3$) concentrate were prepared by adding to a Banbury mixer 67 parts by weight $CaCO_3$ (grade UF, with a mean particle size of 0.8 microns), 0.22 parts by weight of Irganox 1010, 3.3 parts by weight of Kemamide E (an unsaturated fatty monoamide derived from erucic acid and available from Humko Sheffield Chemical Co., Memphis Tenn.) as a slip agent, and 29.48 parts by weight of LDPE (melt index = 10). The foregoing mixture of ingredients was mixed in the Banbury and then pelletized to yield the desired calcium carbonate concentrate.

The base polymer and additives comprising the upper layer of the apertured film cover were then prepared for feeding to a first extruder by mixing 85 parts by weight of Dowlex 2035 with 15 parts by weight of the above-described calcium carbonate concentrate. Dowlex 2035 is a linear low density polyethylene resin which is available from Dow Chemical Company. Typical properties of compression molded samples of this resin are as follows: Melt Index=6.0 gm/10 minutes (ASTM D-1238); Density=0.919 gm/cc (ASTM D-792); Vicat Softening Point=97° C. (ASTM D-1525); Tensile Yield=1700 psi (ASTM D-638, crosshead speed of 20 inches/min.); Ultimate Tensile=2500 psi (ASTM D-638, crosshead speed of 20 inches/min.); Ultimate Elongation=650% (ASTM D-638, crosshead speed of 20 inches/min.); and Flexural modulus, 2% secant=37,000 psi (ASTM D-638). Dowlex 2035 was determined to have a melting point of 124° C. using Differential Scanning Calorimetry.

The base polymer and additives comprising the lower layer of the apertured film cover were then prepared for feeding to a second extruder by dry mixing 85.0 parts by weight of Escorene 721.88 with 15 parts by weight of the above-described $TiO_2$ concentrate. Escorene 721.88 is an ethylene-vinyl acetate (EVA) copolymer resin available from Exxon Chemical Company containing 18% by weight of vinyl acetate and having a nominal melt index of 2.5 dg/min. Typically, the Escorene 721.88 resin has a density of 0.942 $gm/cm^3$ (ASTM D-1505), a melt index of 2.0 dg/min (ASTM D-1238), and a melting point of about 87° C.

All the materials (i.e. the LLDPE base resin and additives) comprising the upper layer were fed through a hopper into the inlet of a first heated extruder and all the materials (i.e. the EVA base resin and additives) comprising the lower layer were fed through another hopper to a second heated extruder. The upper layer materials exited the first extruder in molten form and were delivered through a first melt pump to a heated combining block. The lower layer materials in molten form were delivered through a second melt pump to the same combining block.

Referring to FIG. 5, there is schematically illustrated a process for preparing the two-layered, apertured film of the present invention. Certain portions of the apparatus and processing steps used to produce the apertured film layer are disclosed generally in the prior art, e.g. in U.S. Pat. No. 3,632,269 (Dovlak, et al.) and U.S. Pat. No. 4,381,326 (Kelly).

The melt for the upper layer at a temperature of about 450° F. and the melt for the lower layer at a temperature of about 440° F. were then fed to a dual compartment, heated slot die 50 for coextrusion into a thin sheet. The slot die 50 contains a separator 52 which divides the interior of the die into separate compartments 54 and 56, as shown in FIG. 6. A temperature gradient is developed across the slot die, ranging from 415° F. at the ends to 425° F. at the center. The LLDPE material was extruded through compartment 56, and the EVA material through compartment 54. The thickness ratio of upper layer 42 and lower layer 44 was controlled by the weight outputs of the extruders as applied to the slot die to give a final product which comprised 35% by weight of the upper layer and 65% by weight of the lower layer.

From the slot die 50 the molten sheet 60 of coextruded materials drops directly into a nip 71 between a heated, smooth surfaced roll 70 and a resilient forming roll 72. Forming roll 72 had a resilient outer surface which was engraved with a pattern comprising a series of discontinuous elevated lands 74 separated by a continuous recessed area 84 as shown in exaggerated cross-section in FIG. 5. The shape of the apertures or holes in the apertured coextruded film corresponds generally to the shape of the land portions of the resilient forming roll 72 used in the coextrusion process. These land portions may take any desired geometrical shape such as rectangles, squares, hexagons, triangles, circles and the like. The size and number of lands on the forming roll should be selected to provide sufficient open area in the final apertured coextruded film to allow passage of body fluids, such as menstrual fluid, urine and the like, through the film into the absorbent core beneath. The lands were in the form of uniform hexagons, the sides of which measured 0.0104 inches. The hexagonal lands were 0.0065 inches in height and had a center-to-center spacing of 0.028 inches. Roll 72 rotates at a speed from 1.5% to 8% faster than roll 70. As the rolls 70 and 72 rotate, they draw the coextruded material into nip 71, at which point the rolls cooperate in a wiping action to force substantially all of the coextrudate 60 into the continuous recessed areas 84 of the resilient forming roll 72. Rolls 70 and 72 are aligned to contact each other at an approximate pressure of 65 lbs. per linear inch.

Heated roll 70 has a surface temperature of about 260° F., whereas resilient forming roll 72 was internally cooled by 60° F. water to provide an average surface temperature of about 200° F. The resulting temperature differential between the two rolls, together with the engraved pattern on the forming roll, results in the sheet 60 being drawn around forming roll 72. The molten sheet begins to solidify in the desired form of an apertured film while it is in contact with the forming roll, the apertures of the film assuming the general shape of the lands 74 on the forming roll. It will be understood that the apertures in the film are formed by the action of the raised areas or lands 74 of the forming roll pressing through the molten coextrudate 60 just after it exits slot die 50.

The apertured film product passes from forming roll 72 to a chill roll 76. The chill roll 76 contacts the forming roll 72 at an approximate pressure of 55 lbs. per linear inch and is cooled to a temperature of about 65° F. This brings the temperature of the apertured film to ambient conditions. The film is drawn off of the chill roll 76 by a pair of pull rolls 77 and 78, and the film is then rolled up on a take-up roll 80.

The same general procedure described above was used to make additional apertured films. The formulations for the upper (body-contacting) layer and the lower (absorbent-core contacting) layer of each apertured film are set forth in Table A.

TABLE A

| INGREDIENT (parts by weight) | EX 1 | EX 2 | EX 3 | EX 4 |
|---|---|---|---|---|
| Upper Layer (A) | | | | |
| LLDPE[1] | 28.00 | | | 29.750 |
| HDPE[8] | | | 16.934 | |
| LDPE | | 12.74[6] | | 1.547 |
| Calcium Carbonate | 3.50 | | | 3.517 |
| $TiO_2$, rutile | | 3.00 | 1.482 | |
| Irganox 1010[2] | 0.035 | 0.10 | | 0.011 |
| Erucamide[3] | 0.175 | 0.10 | 0.102 | 0.175 |
| DSTDP[12] | | 0.06 | | |
| Silica Concentrate | | 4.0[7] | | |
| Carrier Resin for $TiO_2$ | | | 1.482 | |
| LLDPE, Carrier for $CaCO_3$[11] | 3.29 | | | |
| Lower Layer (B) | | | | |

TABLE A-continued

| | | | | |
|---|---|---|---|---|
| EVA | 55.25[4] | 66.96 | 68.08[9] | 55.25[10] |
| TiO$_2$, rutile | 4.875 | 6.00 | 5.96 | 4.87 |
| Irganox 1010 | 0.065 | 0.40 | | 0.02 |
| Erucamide | | 0.40 | | |
| DSTDP | | 0.24 | | |
| LDPE, Carrier for TiO$_2$ | 4.810[5] | 6.00 | 5.96 | 4.86 |
| Wt. Ratio, (A):(B) | 35:65 | 20:80 | 20:80 | 35:65 |

FOOTNOTES TO TABLE A
[1]Dowlex 2035 from Dow Chemical Co.
[2]Irganox 1010 is an anti-oxidant commercially available from Ciba-Geigy.
[3]Erucamide is a slip agent available from Humko Sheffield Chemical Co. as Kemamide E.
[4]EVA copolymer resin available from Exxon Chemicals under the designation Escorene 721.62. This resin contains about 18% by weight of vinyl acetate and a nominal melt index of 2.5 dg/min. Typically, according to information published by the supplier, this resin has a density of 942 kg/m$^3$ (ASTM D-1505), a melt index of 2.0 dg/min. (ASTM D-1238), and a melting point of about 87° C. We determined the melting point of this resin to be 88° C. using Differential Scanning Calorimetry.
[5]Nominal melt index = 10 (ASTM D-1238, condition E)
[6]LDPE available from U.S. Industries as Petrothene NA-151. We determined the melting point of this resin to be 101° C. using Differential Scanning Calorimetry.
[7]20% by weight of diatomaceous silica and 80% by weight of LDPE carrier resin having a melt index of 9 and a density of 0.918 gm/cc.
[8]Dowlex 04052N available from Dow Chemical Company. Typical properties of compression molded samples of this resin are as follows: Melt Index = 4.0 gm/10 min. (ASTM D-1238); Density = 0.952 gm/cc (ASTM D-792); Vicat Softening Point = 123° C. (ASTM D-1525); Tensile Yield = 3650 psi (ASTM D-638); Ultimate Tensile = 3750 psi (ASTM D-638); Ultimate Elongation = 1000% (ASTM D-638); Flexural Modulus, 2% secant = 145,000 psi (ASTM D-638). We determined the melting point of Dowlex 04052N to be 135° C. using Differential Scanning Calorimetry.
[9]EVA copolymer resin containing about 18% by weight of vinyl acetate and available from E. I. duPont as Elvax 460. The physical properties of this resin are generally equivalent to those set forth in 4 above for Escorene 721.62. We determined the melting point of Elvax 460 to be 89° C. using Differential Scanning Calorimetry.
[10]EVA copolymer resin containing about 18% by weight vinyl acetate and available from Exxon Chemicals under the designation Escorene 721.88. Physical properties of this particular resin are substantially the same as those set forth in 4 above for Escorene 721.62. We determined the melting point of Escorene 721.88 to be 88° C. using Differential Scanning Calorimetry.
[11]Nominal melt index = 18.
[12]Distearyl thio dipropionate.

FIG. 7 shows the cover material in cross-section, including the polyethylene (PE) layer 42 overlaying the ethylene vinyl acetate (EVA) layer 44. This two layer structure provides an ease in thermal sealing by virtue of the melting point temperature differential between the two layers. When the cover is thermally bonded to the barrier as shown at 22 in FIG. 2, the cover is heated to a temperature at or above the melting point of the EVA layer but below the melting point of the PE layer. The molten EVA layer bonds to the barrier, while the structurally sound PE layer maintains web integrity while the EVA layer is in its molten condition. The PE layer thus maintains the uniform webbed structure of the cover so that the cover is not disfigured at the thermally bonded edges.

It is believed that a major reason for the strong integrity exhibited by the coextruded apertured film of FIG. 7 is the fact that at the top layer 42 not only overlays the bottom layer 44, but also tapers into and lines the holes 46 in the web. This structure was confirmed by performing microscopic examination on a cross-sectioned sample of the apertured film, which was stained with 3% Sudan IV and propanol. Referring to FIG. 7, the film of the present invention includes a large plurality of apertures 46 which are defined by interiorly located walls 48 of the film. The height of the apertures is substantially equivalent to the thickness of the film, i.e. the apertures extend from the exposed surface 42' of upper layer 42 through the film to the exposed surface 44' of lower layer 44. The composition of the interiorly located walls which define the apertures corresponds substantially to the chemical composition (i.e. the base resin and additives) of the upper layer of the film. In other words, the interior walls which define the plurality of apertures are a continuation of the upper layer of the film. The web resists tearing and disfigurement by reason of the circumferential lining of the holes 46 by the top layer. Even when the bottom layer is molten during sealing, the hole shape is preserved by this unmelted lining. Tearing is also resisted by the integrity of the circumferential lining.

As FIG. 7 shows, the two layers of the cover are of different thicknesses. The choice of the ratios of the layer thicknesses is dependent upon their melting point temperature differential. In general, the smaller the melting point temperature differential, the greater the thickness of the top layer that is need to maintain web integrity, that is, the greater the ratio of the top layer to bottom layer thickness. The following table B shows a number of material ratios and temperature differentials that were tried.

TABLE B

| Composition Top Layer/Bottom Layer | Layer Ratio Top %/Bottom % | Melting Point Temperature Difference |
|---|---|---|
| HDPE/EVA | 20/80 | 47° C. |
| LLDPE/EVA | 50/50 | 36° C. |
| LLDPE/EVA | 35/65 | 36° C. |
| LLDPE/EVA | 20/80 | 36° C. |
| LDPE/EVA | 35/65 | 13° C. |
| LDPE/EVA | 20/80 | 13° C. | where HDPE=high density polyethylene; EVA=ethylene vinyl acetate; LLDPE=linear low density polyethylene; and LDPE=low density polyethylene.

Consistent with the above criterion, the compositions at the top of Table B exhibited better characteristics than those at the bottom. It was found that a composition should preferably satisfy the following condition in order to have acceptable heat sealing characteristics:

$$\frac{58.6e^{[-5.14(10)-2(X)]}}{Y} \leq 1.0$$

where X=the weight percent of the top layer, and Y=the melting point temperature differential of the two materials (melting point of top layer minus melting point of bottom layer). The preferred composition of a 35%/65% ratio of LLDPE/EVA satisfies this condition: Compositions which do not meet the preferred melting point temperature differential and layer ratio criterion were found to cut at stress points in the cover when exposed to the heat and pressures of the thermal sealing operation.

It should be noted that the above mathematical expression is applicable for a particular thermal sealing operation, and is based upon numerous processing parameters, such as the speed of the operation, temperature control parameters, material stresses, etc. Different processes may be characterized by different forms of this expression, in which the constant term of 58.6 is representative of the particular processing parameters. In general, as thermal sealing techniques are refined and improved, the value of the constant term will decrease, allowing a greater variety of materials with lower melting point temperature differentials and top layer weight percents to qualify as being within acceptable limits.

A typical thermal sealing process for the sanitary napkin of the present invention is schematically illustrated in FIG. 8. The napkin components are moved to the sealing process on a delivery conveyor 90, with the cover 14 on the bottom with the top layer 42 facing downward, absorbent pads 12 located on the cover, and the barrier 16 on the top. The materials are delivered to the nip between two heated rolls, a metal roll 92 and a silicone rubber coated roll 98. The metal roll 92 contains several non-sealing pad cavity areas 96 which are surrounded and separated by seal face areas 94. The rolls are heated to a temperature at or above the melting point of the bottom (EVA) layer, but below the melting point temperature of the top (LLDPE) layer. The two rolls interfere by about 0.015 inches as shown at 104 when the seal face areas meet the rubber coated roll to seal the cover to the barrier. The pads are aligned to pass between the rolls in the pad cavities. The thermally sealed areas are shown at 100, as the sealed napkins leave the sealing process by way of a take-off conveyor 102. The finished napkins may then be separated for subsequent packaging.

It has been discovered that the coextruded apertured film of the present invention exhibits a preference for fluid flow in a direction from the top layer to the bottom layer and a tendency to retard fluid flow in the opposite direction. This discovery is particularly surprising in that the phenomenon is superior to that of an apertured film comprised of a single material. To illustrate this phenomenon, samples of LLDP/EVA apertured film of the present invention were held in three inch diameter hoops, first with the top layer directed upward. Means including an eyedropper and a syringe pump were used to deposit up to ten drops of a saline solution containing blue dye on the top layer surfaces of the samples. Commencing with the time of application of the first drop, the elapsed time until a drop of solution fell from the underside of the material was noted. The cover material samples were then inverted so that the bottom layer was directed upward. The same procedure was followed to determine the number of drops and elapsed time required to penetrate the material and fall from the downward-directed top layer. The results showed that only a few drops were required before the solution penetrated from the top layer through the bottom layer and fell from the material, whereas significantly more drops were required to penetrate the cover material in the opposite direction. In many cases, the cover material was not penetrated in the bottom to top direction by the full application of ten drops of solution.

What is claimed is:

1. An absorbent product, including a body of absorbent material covered by a cover of polymeric materials, said cover comprising:
   a first layer of polymeric material which exhibits a first melting point temperature;
   a second layer of polymeric material, bonded to said first layer, said second layer exhibiting a second melting point temperature which is less than said first melting point temperature; and
   a plurality of apertures, penetrating through both said first layer and said second layer for the transmission of fluids through said cover,
   wherein said first layer maintains the integrity of said apertured cover when said cover is heated to a temperature below said first melting point temperature for thermal bonding of said cover.

2. The absorbent product of claim 1, further compromising a fluid impervious barrier, said second layer of said aperture film cover being thermally bonded to said barrier,
   wherein said cover and said barrier enclose said absorbent material with said first layer comprising an outer surface of said absorbent product.

3. The absorbent product of claim 2, wherein said second layer of polymeric material includes a colorant compound.

4. The absorbent product of claim 3, wherein said polymeric material of said first layer includes a delustrant compound.

5. The absorbent product of claim 4, wherein said polymeric material of said first layer includes a slip agent, said slip agent being substantially absent from said polymeric material of said second layer.

6. The absorbent product of claim 1, wherein said polymeric material of said first layer circumferentially lines the inner surfaces of said apertures.

7. The absorbent product of claim 6, wherein said polymeric materials of said first and second layers are chosen from the class of lower polyolefins having from two to four carbon atoms per repeating unit.

8. The absorbent product of claim 7, wherein said first layer exhibits a first thickness, and said second layer exhibits a second thickness, the thickness of said first layer relative to the thickness of said second layer being determined in relation to the difference in melting point temperatures of said two polymeric materials, said first to second layer thickness ratio varying inversely in relation to said melting point temperature difference.

9. The absorbent product of claim 8, wherein said polymeric material of said first layer comprises polyethylene and said polymeric material of said second layer comprises ethylene vinyl acetate.

10. In a product for absorbing body fluids and having an absorbent core and a body fluid permeable cover overlying said core, wherein said cover comprises:
    a polymeric film having a plurality of small apertures for the transmission of body fluids therethrough; said film comprising an upper layer to be placed against the body and a lower layer placed against a first side of said absorbent core; said upper layer comprising a first polymeric material and said lower layer comprising a second polymeric material; said first polymeric material having a melting point which is higher than the melting point of said second polymeric material, said cover being secured to said product by thermal bonding.

11. The product of claim 10, wherein said apertures are defined by interiorly located walls of the film, said walls being a continuation of said upper layer.

12. The product of claim 11, wherein the weight percent of said first polymeric material based on the weight of said first and second polymeric materials is selected in inverse proportion to the melting point temperature differential of the first and second polymeric materials.

13. The product of claim 12, wherein said first polymeric material is selected from the group consisting of lower polyolefins having from two to four carbon atoms per repeating unit, nylon. or ethyl acrylate/ethylene copolymer; and said second polymeric material is selected from the group consisting of lower polyolefins having from two to four carbon atoms per repeating unit, ethylene/vinyl acetate copolymer, methyl acrylate/ethylene copolymer, acrylic acid/ethylene or copolymer.

14. The product according to claim 13, wherein said first polymeric material comprises a major amount of a polymer selected from the group consisting of low density polyethylene, high density polyethylene, and linear low density polyethylene.

15. The product according to claim 13, wherein said second polymeric material comprises a major amount of an ethylene vinyl acetate copolymer.

16. The product according to claim 13, wherein said first polymeric material comprises a major amount of linear low density polyethylene and said second polymeric material comprises a major amount of an ethylene vinyl acetate copolymer.

17. The product according to claim 16, wherein the weight ratio of said upper layer to said lower layer ranges from 85:15 to 10:90.

18. The product according to claim 17, wherein the weight ratio of said upper layer to said lower layer ranges from 50:50 to 20:80.

19. The product according to claim 10, wherein said upper layer contains a delustrant and said lower layer contains an opacifier.

20. The product according to claim 19, wherein the delustrant in said upper layer is calcium carbonate, and the opacifier in said lower layer is titanium dioxide.

21. The product according to claim 10, further comprising a fluid impervious barrier placed against a second side of said absorbent core, said lower layer of said apertured film cover being thermally bonded to said barrier.

22. The product of claim 10 as a disposable diaper.

* * * * *

UNITED STATES PATENT AND TRADEMARK OFFICE
CERTIFICATE OF CORRECTION

PATENT NO.   : 4,690,679
DATED        : September 1, 1987
INVENTOR(S)  : William B. Mattingly, III  et al.

It is certified that error appears in the above-identified patent and that said Letters Patent is hereby corrected as shown below:

Col. 12, lines 8 and 9:  "compromising" should be --comprising--.

Col. 12, line 10:  "aperture" should be --apertured--.

Col. 13, line 2 :  "nylon." should be --nylon,--.

Signed and Sealed this

Twenty-seventh Day of September, 1988

Attest:

DONALD J. QUIGG

*Attesting Officer*            *Commissioner of Patents and Trademarks*